(12) United States Patent
Fujita et al.

(10) Patent No.: US 6,679,099 B2
(45) Date of Patent: Jan. 20, 2004

(54) GAS SENSOR

(75) Inventors: Yasuhiro Fujita, Gifu (JP); Makoto Togawa, Gifu (JP); Yoshiaki Matsubara, Aichi (JP)

(73) Assignee: NGK Spark Plug Co., Ltd., Nagoya (JP)

( * ) Notice: Subject to any disclaimer, the term of this patent is extended or adjusted under 35 U.S.C. 154(b) by 0 days.

(21) Appl. No.: 10/318,912

(22) Filed: Dec. 13, 2002

(65) Prior Publication Data
US 2003/0150254 A1 Aug. 14, 2003

(30) Foreign Application Priority Data

Dec. 28, 2001 (JP) ........................................ 2001-400578

(51) Int. Cl.[7] ............................................... G01N 19/10
(52) U.S. Cl. ....................................................... 73/23.2
(58) Field of Search .............................. 73/23.2, 31.05; 204/402, 415, 431; 148/282, 432; 429/220

(56) References Cited
FOREIGN PATENT DOCUMENTS

| JP | 2001-133431 | 5/2001 | |
|---|---|---|---|
| JP | 05149914 | * 6/2003 | ................ 204/431 |

* cited by examiner

Primary Examiner—Hezron Williams
Assistant Examiner—Jay Politzer
(74) Attorney, Agent, or Firm—Brinks Hofer Gilson & Lione (57) ABSTRACT

A gas sensor includes a detection element for detecting a gas component of a gas to be measured, a casing for holding the detection element and a seal member forming a reference gas space together with the casing. The seal member has an end surface exposed to the atmosphere and a through-hole for establishing communication between the atmosphere and the reference gas space. A cylindrical insert member is inserted in the through-hole of the seal member. A sheetlike air permeable filter is sandwiched between an inner surface of the through-hole of the seal member and the cylindrical insert member so as to cover an atmosphere side opening portion of the cylindrical insert member. The atmosphere side opening portion of the cylindrical insert member is retracted from the end surface of the seal member toward the interior of the through-hole, whereby an atmosphere side face of the air permeable filter is retracted from the end surface of the seal member.

10 Claims, 7 Drawing Sheets

GAS SENSOR

BACKGROUND OF THE INVENTION

1. Field of the Invention

The present invention relates to a gas sensor attached to a pipe which forms a flow path for a gas to be measured and adapted to detect a gas component of the gas to be measured by use of the air introduced therein as a reference gas.

2. Description of the Related Art

Conventionally known gas sensors for detecting the concentration of a specific gas component in a mixed gas include HC sensors and $N_x$ sensors.

One type of an HC or $NO_x$ gas sensor is designated an outside air introduction sensor. This type of gas sensor includes a seal member located in its upper portion which includes an opening formed therein for introducing outside air into the gas sensor. An air permeable filter is disposed in the aperture and prevents entry of dust and water into the sensor. Since the filter is located away from the hot portion of the sensor, that is, that lower portion including a heater and that portion which is exposed to the measured gas, such as hot exhaust gas, thermal deterioration of the filter is prevented. The air permeable filter is sandwiched between an outer circumferential surface of a cylindrical insert and the inner surface of the aperture to partially close the aperture while maintaining air permeability but precluding entry of water. In such a gas sensor, in order to ensure air permeability which might be compromised by water, oil, dust or the like lodged in the opening, the filter generally projects a short distance from the atmosphere side face of the seal member. Thus, even if water, oil, dust or the like adheres to the filter, such substances will typically fall away and the air permeable portion of the gas sensor will maintain its impermeability to water and oil. The outward projection of the filter element prevents accumulation of dust on the filter and maintains good air permeability and performance of the sensor.

Nonetheless, such an outward projection of the air permeable filter from the adjacent seal member of the sensor may render it susceptible to damage when it is mounted in certain locations on the vehicle since it may be exposed to high pressure water utilized in washing the vehicle or may be exposed to a flipped stone which may break the filter resulting in serious damage to the gas sensor and compromised performance.

SUMMARY OF THE INVENTION

The present invention addresses and solves the above-mentioned problem. An object of the invention is to provide a gas sensor in which an air permeable filter is fixed to a seal member by use of a cylindrical insert member and which can prevent breakage of the air permeable filter and entry of foreign matter and can ensure air permeability of the air permeable filter.

To achieve the above object, the present invention provides a gas sensor comprising a seal member which, together with a casing, forms a reference gas space, and being configured such that a cylindrical insert member covered with a sheetlike air permeable filter is inserted into a through-hole formed in the seal member in such a manner as to extend between the atmosphere and the reference gas space. Thus, an atmosphere-side opening portion of the cylindrical insert member is closed with the air permeable filter, and the air permeable filter is fixedly sandwiched between the inner surface of the through-hole of the seal member and the outer surface of the cylindrical insert member. Passing through the air permeable filter, outside air is introduced into the reference gas space via an air path formed in the cylindrical insert member in such a manner as to extend between the atmosphere side opening portion and a reference gas side opening portion of the cylindrical insert member.

The atmosphere side opening portion of the cylindrical insert member is retracted from an end surface of the seal member, which is exposed to the atmosphere, toward the interior of the through-hole of the seal member, whereby the atmosphere side face of the air permeable filter is located within the interior of the seal member; i.e., is retracted from the end surface of the seal member.

Thus, the seal member intercepts high pressure water or a flipped stone directed toward the air permeable filter from the outside, thereby effectively preventing breakage of the air permeable filter. Therefore, the air permeable filter can favorably maintain impermeability to water, oil and the like and air permeability, thereby ensuring reliability of the gas sensor.

The seal member may be a cylindrical ceramic body whose inner and outer circumferential surfaces are covered with sheet rubber. Preferably, the entire seal member is formed of an elastic body such as a rubber member.

The thus formed seal member can absorb impact, to some extent, induced by impingement of high pressure water or a flipped stone, thereby alleviating impact on the air permeable filter fixedly disposed within the seal member and thus effectively preventing breakage of the air permeable filter.

The through-hole may extend through the seal member while its diameter is held constant. However, a through-hole of large diameter encounters difficulty in preventing entry of high pressure water or a flipped stone therein, whereas a through-hole of small diameter involves impaired air permeability. Also, since the cylindrical insert member is generally formed through deep drawing or like working, reduction of its diameter is limited for working related reasons, and thus reduction of the diameter of the through-hole is limited.

Thus, preferably, the through-hole of the seal member is constituted by a small hole opening to the atmosphere and a large hole opening to the reference gas space, the small hole and the large hole communicating with each other. The large hole has a diameter substantially equal to the outside diameter of the cylindrical insert member, and the small hole has a diameter smaller than that of the large hole.

The thus configured through-hole has an advantage that the small hole prevents entry of high pressure water or a flipped stone therein, while the large diameter can receive the cylindrical insert member. The cylindrical insert member abuts a step that is formed between the small hole and the large hole.

The diameters of the small and large holes are determined in view of, for example, suppression of entry of water and oil droplets and a required flow rate of air between the atmosphere and the reference gas space.

Meanwhile, the above mentioned configuration of the present invention requires the accommodation of the cylindrical insert member in the seal member. Generally, the seal member is elastically fixed between the casing and the cylindrical insert member through crimping of the casing from the outside. Therefore, preferably, the cylindrical insert member is present at least at a position corresponding to a portion of the seal member subjected to crimping. Also, in order to impose a certain crimping force or greater on the seal member, the seal member must be subjected to crimping along a predetermined length or longer.

Thus, in order to implement the above mentioned configuration of the present invention, the axial length of the seal member must be rendered longer than that of the cylindrical insert member. However, increasing the length of the casing accordingly is contrary to demand for compactness of a gas sensor. In this case, axially elongating only the seal member is possible. However, thermal expansion of the elongated seal member in the course of using the gas sensor at high temperature induces local stress at a portion of the seal member in contact with an end portion of the casing, potentially resulting in breakage of the seal member at the contact portion.

Therefore, preferably, the seal member has a protrusion axially protruding from the atmosphere side end face thereof, and an atmosphere-side opening portion of the cylindrical insert member is inserted into the protrusion.

Employment of the protrusion allows the seal member to be fixedly disposed between the casing and the cylindrical insert member in a stable condition while the cylindrical insert member is accommodated in the interior of the seal member. Thus, the above-mentioned configuration of the present invention can be effectively implemented.

According to the above-mentioned configuration of the present invention, the cylindrical insert member is fixedly disposed in the interior of the seal member to thereby dispose the air permeable filter within the through-hole of the seal member. Thus, depending on the size of the through-hole or the installation environment of the gas sensor, water, oil or the like may accumulate in a recess defined by the atmosphere side face of the air permeable filter and the wall of the through-hole, resulting in a failure to maintain air permeability.

Therefore, preferably, one or more drain grooves are formed on the atmosphere side end face of the seal member in such a manner as to extend radially outward from the periphery of the atmosphere side face of the air permeable filter, so as to drain radially outward water or oil adhering to the atmosphere side face.

Employment of the drain groove prevents a problem in that adhering water or oil stagnates on the atmosphere side face of the air permeable filter, thereby ensuring air permeability and thus maintaining good gas sensor performance.

Preferably, the bottom surface of the drain groove is located in such a manner as to be biased toward the reference gas space in relation to the atmosphere side face of the air permeable filter. This feature of the drain groove enhances radially outward drainage of water or oil via the drain groove particularly when the gas sensor is installed such that a proximal end portion thereof faces upward.

DESCRIPTION OF THE PREFERRED EMBODIMENTS

Figure 9:
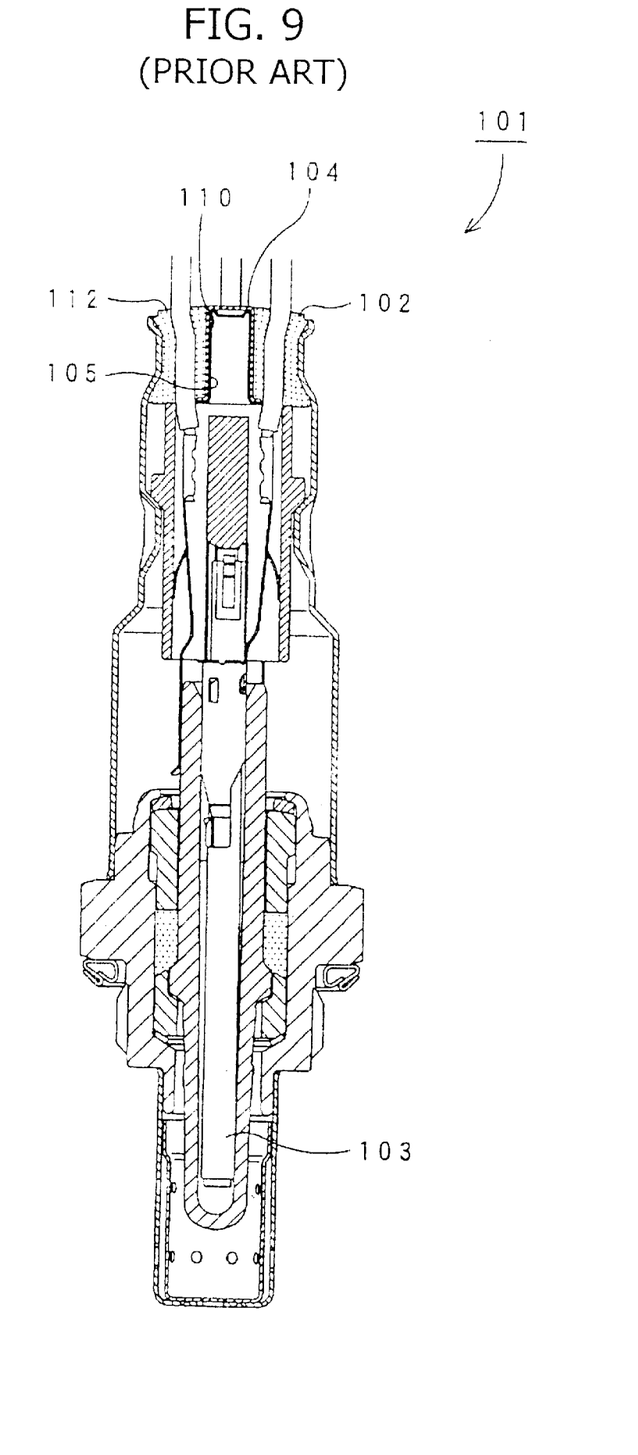
FIG. 9 is a sectional view showing the overall configuration of a conventional, prior art oxygen sensor.

FIG. 9 shows an example of a conventional, i.e., prior art, gas sensor; i.e., a gas sensor 101 of an outside air introduction type. A seal member 102 is disposed at an upper portion of the gas sensor 101 and has a through-hole 110 formed therein for introducing outside air into the gas sensor 101. An air permeable filter 104 is disposed in the through-hole 110 and prevents entry of dust and water into the gas sensor 101. Since the air permeable filter 104 is located away from a hot portion of the gas sensor 101 (i.e., a lower portion of the gas sensor 101 including a heater 103 (heat source) and a portion exposed to hot gas such as exhaust gas), thermal deterioration of the air permeable filter 104 is prevented. In assembly of the gas sensor 101, a cylindrical insert member 105 covered with the sheetlike air permeable filter 104 is inserted into the through-hole 110. The air permeable filter 104 is fixedly sandwiched between the outer circumferential surface of the cylindrical insert member 105 and the inner circumferential surface of the through-hole 110 to thereby close the through-hole 110 while air permeability is maintained and entry of water is prevented.

In the gas sensor 101, in order to prevent impairment in air permeability which might otherwise result from water, oil, dust, or the like caught in the through-hole 110, the air permeable filter 104 generally protrudes by a predetermined height from an atmosphere side end face 112 of the seal member 102. Thus, even when water, oil, or the like adheres to the air permeable filter 104, such an adhering substance does not continue adhering, whereby an air permeation portion of the gas sensor 101 can maintain impermeability to water and oil. The outward protrusion of the air permeable filter 104 prevents accumulation of dust on the air permeable filter 104, thereby maintaining good air permeability of the air permeable filter 104 and thus maintaining required performance of the gas sensor 101.

However, the outward protrusion of the air permeable filter 104 from the seal member 102 potentially involves the following problem. For example, when the gas sensor 101 mounted on a vehicle is exposed to the exterior of a vehicle body, high pressure water used in washing the vehicle or a flipped stone may hit and break the air permeable filter 104, resulting in fatal damage to the gas sensor 101 in terms of performance.

Embodiments of the present invention will next be described in detail with reference to the drawings.

Figure 1:
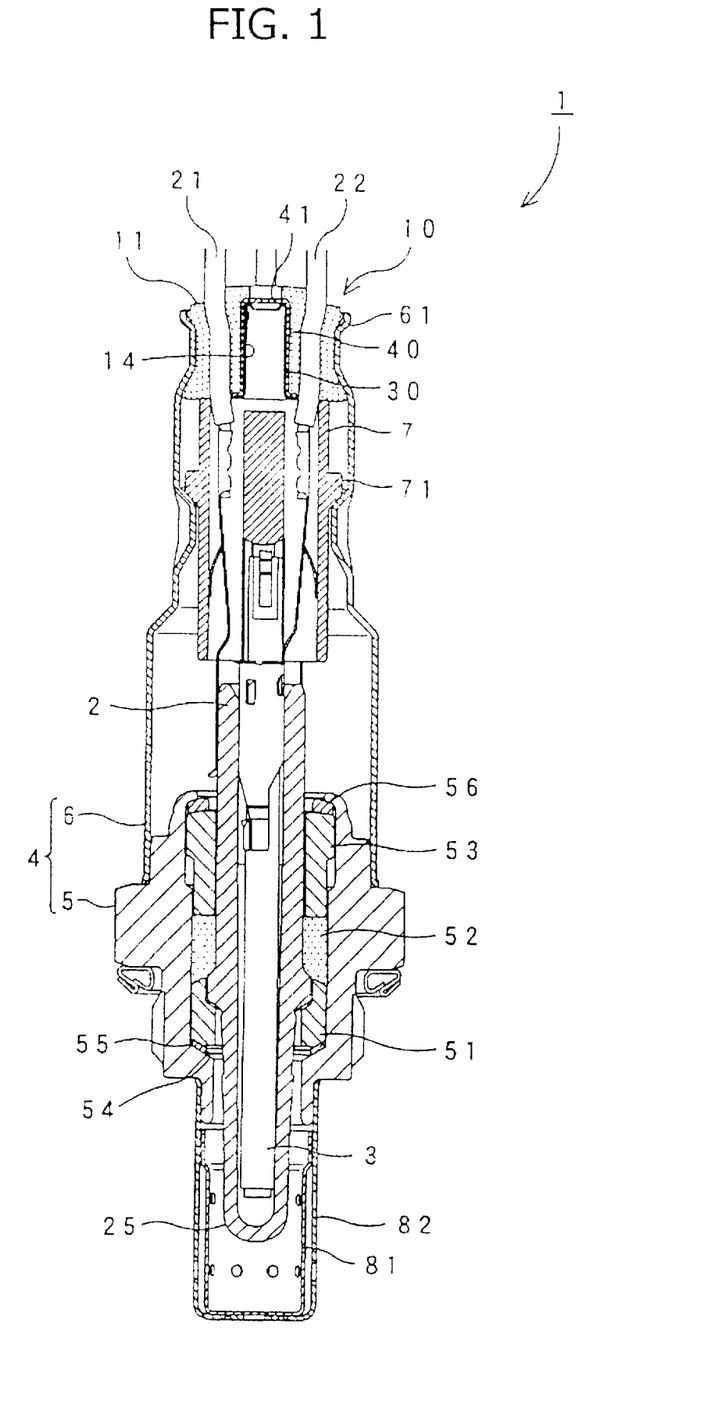
FIG. 1 is a full, sectional view showing the overall configuration of an oxygen sensor according to a first embodiment of the present invention.

The first embodiment of a gas sensor according to the present invention is configured to serve as an oxygen sensor. FIG. 1 schematically shows the configuration of the oxygen sensor 1. In this embodiment, the lower end of the oxygen sensor 1 corresponds to the "distal end of the gas sensor"

appearing in the appended claims, and the upper end of the oxygen sensor 1 corresponds to the "proximal end of the gas sensor."

As shown in FIG. 1, the oxygen sensor 1 includes a detection element 2 formed of a solid electrolyte body having a hollow rodlike form with a distal end which contains a predominant amount of $ZrO_2$; a rodlike ceramic heater 3 disposed within the detection element 2; and a casing 4 adapted to accommodate an internal structure of the oxygen sensor 1 and fixedly attached to an exhaust pipe or the like to thereby mount the oxygen sensor 1 in place.

The casing 4 includes a metallic shell 5 for holding the detection element 2 and for extending a detection portion 25 of the detection element 2 into the interior of an exhaust pipe or the like; and a cylindrical member 6 extending upward from the metallic shell 5 and forming a reference gas space between the same and the detection element 2.

The metallic shell 5 accommodates a support member 51 having a cylindrical body which supports the detection element 2 from underneath; a filling member 52 formed from talc powder which fills a space located above the support member 51; and a sleeve 53 pressing the filling member 52 from above.

Specifically, a stepped portion 54 is provided at a lower end portion of the metallic shell 5 in such a manner as to protrude inward from the inner circumferential surface of the lower end portion. The support member 51 rests on the stepped portion 54 via a ring 55, thereby supporting the detection element 2 from underneath. The filling member 52 is disposed in a space located above the support member 51 and between the inner circumferential surface of the metallic shell 5 and the outer circumferential surface of the detection element 2. Further, in a coaxial condition, the cylindrical sleeve 53 is placed on the filling member 52, and a ring 56 is placed on the cylindrical sleeve 53. While these components are in place within the metallic shell 5, an upper end portion of the metallic shell 5 is crimped inward (downward), thereby compressing the filling member 52 and thus firmly securing the detection element 2 in relation to the metallic shell 5.

Then, a lower opening end portion of the cylindrical member 6 is fitted onto the metallic shell 5 in such a manner as to cover an upper opening end portion of the metallic shell 5. Subsequently, the lower opening end portion of the cylindrical member 6 is welded from the outside to the metallic shell 5, thereby forming a unitary assembly of the cylindrical member 6 and the metallic shell 5.

A cylindrical, electrically insulative separator 7 of ceramic is disposed within the cylindrical member 6 in the vicinity of an upper opening end portion 61 of the cylindrical member 6. The separator 7 has a flange portion 71 protruding outward from an axially central portion of the outer circumferential surface thereof. By crimping the cylindrical member 6 from the outside at an upper portion thereof, the separator 7 is held within the cylindrical member 6 while the lower end face of the flange portion 71 rests on the crimped portion of the cylindrical member 6.

Further, a seal unit 10 is provided at the upper opening end portion 61 of the cylindrical member 6. The seal unit 10 is adapted to provide a seal between the exterior of the oxygen sensor 1 and a pair of lead wires 21 and 22 connected to corresponding electrodes of the detection element 2 and a pair of lead wires connected to the ceramic heater 3 and to prevent entry of water and oil into the oxygen sensor 1.

A double structure composed of metallic protectors 81 and 82 each having a plurality of holes formed therein is welded to a lower end portion of the metallic shell 5 while covering a portion of the detection element 2 protruding from the metallic shell 5.

Next, the structure of the seal unit 10, which is an essential portion of the oxygen sensor 1 of the present invention and the periphery of the seal unit 10 will be described in detail with reference to FIGS. 2 to 5.

Figure 2:
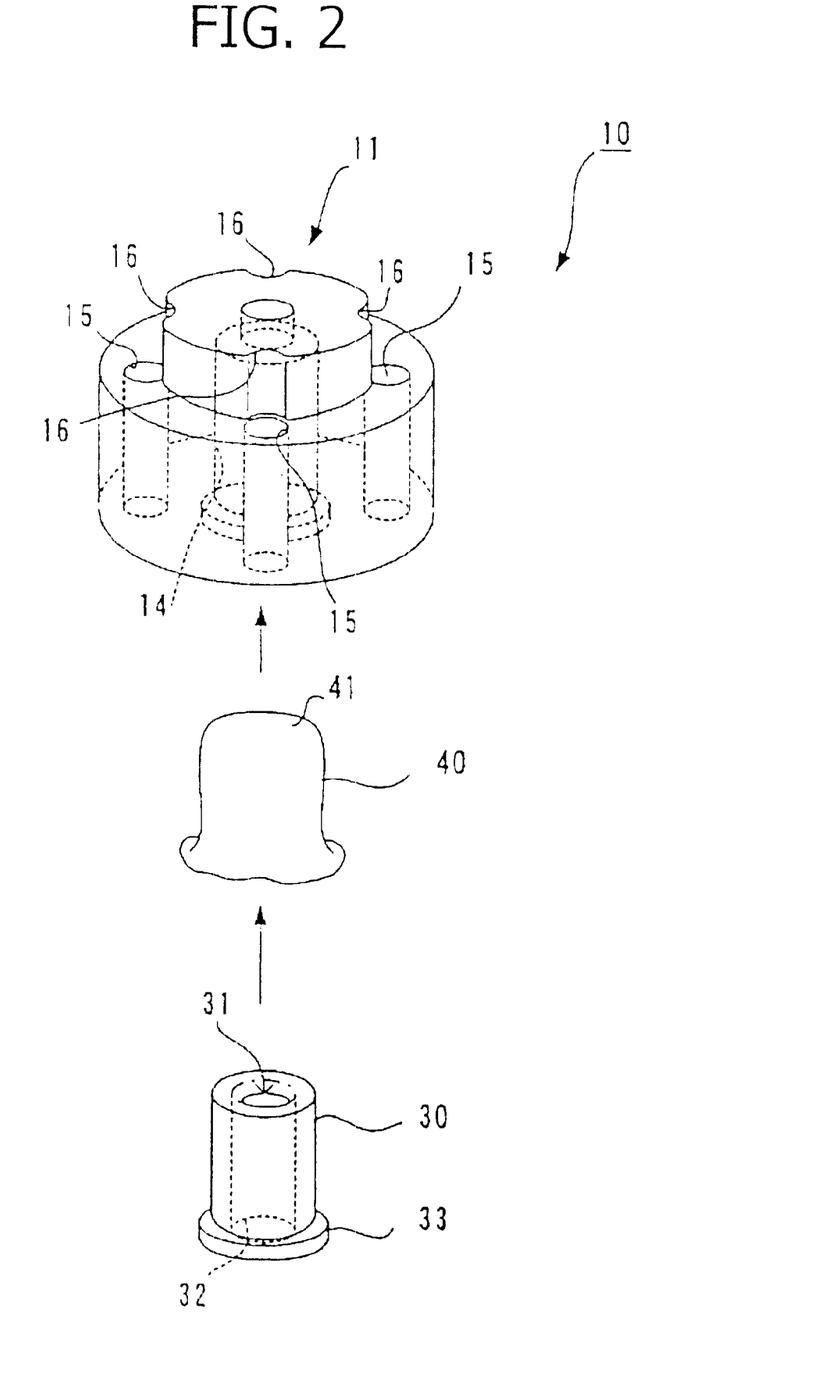
FIG. 2 is an exploded, perspective view of a seal unit of the oxygen sensor of the first embodiment.
Figure 3:
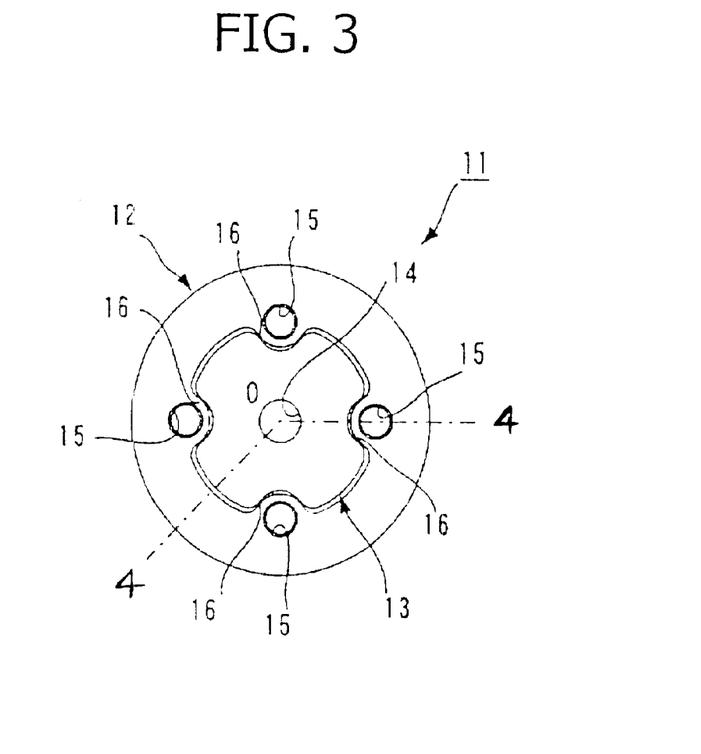
FIG. 3 is a plan view of a seal member of the seal unit of FIG. 2.
Figure 4:
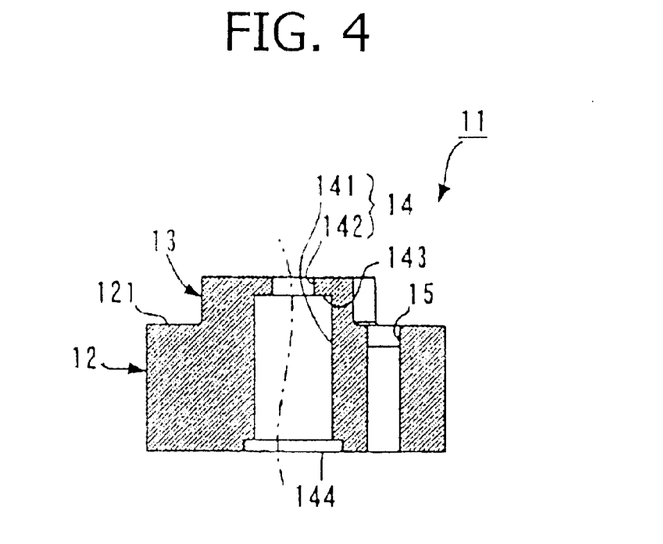
FIG. 4 is a sectional view of the seal member taken along line 4—4 of FIG. 3.
Figure 5:
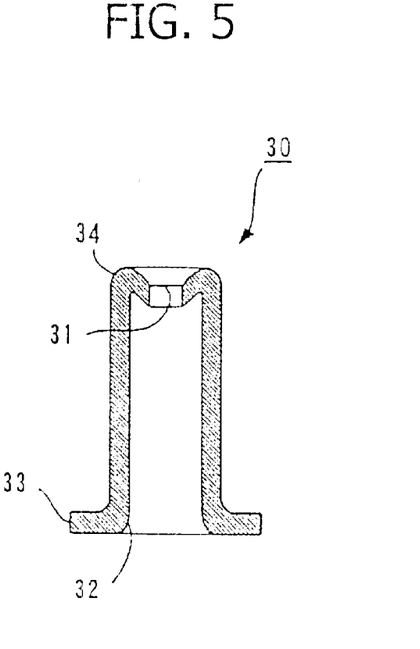
FIG. 5 is a full, sectional view of a cylindrical insert member of the seal unit of FIG. 2.

As shown in FIG. 2, the seal unit 10 includes a columnar seal member 11 formed from fluorine-containing rubber; a cylindrical insert member 30 capable of being inserted into a through-hole 14 extending through the seal member 11 along the axis of the seal member 11; and a sheetlike air permeable filter 40 fixedly sandwiched between the inner circumferential surface of the through-hole 14 and the outer circumferential surface of the cylindrical insert member 30 while covering an upper end portion (an atmosphere side portion) of the cylindrical insert member 30. FIG. 3 is a plan view of the seal member 11; FIG. 4 is a sectional view of the seal member 11 taken along line 4—4 of FIG. 3; and FIG. 5 is a sectional view of the cylindrical insert member 30.

As shown in FIGS. 3 and 4, the seal member 11 includes a columnar body 12 and a protrusion 13, which protrudes from an upper face 121 (an atmosphere side face) of the body 12 along the axis of the seal member 11. The through-hole 14 is formed in the seal member 11 in such a manner as to extend through the body 12 and the protrusion 13 along the axis of the seal member 11. Four lead passage holes 15 are formed in the body 12 while being arranged at equal intervals about a predetermined circle concentric with the through-hole 14, for allowing the lead wires 21 and 22 and the paired lead wires mentioned above to pass therethrough. Axially extending semicircular recesses 16 are formed on the outer circumferential surface of the protrusion 13 at positions corresponding to the four lead passage holes 15, thereby allowing the above-mentioned lead wires to run upward, after passing through the corresponding four lead passage holes 15.

As shown in FIG. 4, the through-hole 14 is formed such that a large hole 141 opening to the reference gas space and having a diameter substantially equal to the outside diameter of the cylindrical insert member 30 and a small hole 142 opening to the atmosphere and having a diameter smaller that of the large hole 141 axially communicate with each other. Thus, a step 143 is formed between the large hole 141 and the small hole 142. In the present embodiment, the step 143 is formed at a position higher than the upper face 121 of the body 12. Further, a circular recess 144 having a diameter greater than that of the large hole 141 is formed at a reference gas side opening portion of the large hole 141. Thus, the cylindrical insert member 30 inserted into the through-hole 14 from underneath is fitted in the seal member 11 while abutting the step 143 and being engaged with the circular recess 144.

In the present embodiment, in order to effectively suppress entry of a water droplet or an oil droplet into the small hole 142, the small hole 142 is formed so as to have a diameter of about 1 to 2 mm and a depth of about 1 to 2 mm.

As shown in FIGS. 2 and 5, the cylindrical insert member 30 is opened at opposite ends to thereby form an atmosphere-side opening portion 31 and a reference gas side opening portion 32, and assumes a cylindrical form that can be inserted into the through-hole 14. A flange portion 33 extends radially outward from the end of the reference gas side opening portion 32.

Formation of the atmosphere side opening portion 31 is described in more detail. An atmosphere side end portion of the cylindrical insert member 30 is bent radially and axially inward, whereby the thus bent portion forms the atmosphere-side opening portion 31. As a result, a radiused end 34 is formed at the atmosphere side end portion of the cylindrical insert member 30. Also, a predetermined space is formed between the inwardly bent portion of the cylindrical insert member 30 and the surface of the air permeable filter 40 covering the atmosphere side end portion of the cylindrical insert member 30.

The air permeable filter 40 is formed from a porous fabric (e.g., GORE-TEX, trade name of product of Japan Gore-Tex Inc.) which is obtained by, for example, stretching a green body of polytetrafluoroethylene (PTFE) at a temperature higher than the melting point of PTFE. Thus, the air permeable filter 40 is impermeable to liquid which contains a predominant amount of water, such as water droplets, and permeable to gas (such as air and water vapor). Further, a porous fabric coated with an oil repellent (e.g., OLEO VENT FILTER, trade name of product of Japan Gore-Tex Inc.) may be used, thereby diminishing the possibility of entry of oil vapor formed through vaporization of adhering oil.

As shown in FIG. 2, in assembly of the seal member 11, the air permeable filter 40, and the cylindrical insert member 30, while being covered with the air permeable filter 40 such that an atmosphere side end portion and the outer circumferential surface thereof are covered with the air permeable filter 40, the cylindrical insert member 30 is inserted into the through-hole 14. Thus, the air permeable filter 40 is fixedly sandwiched between the outer circumferential surface of the cylindrical insert member 30 and the inner circumferential surface of the through-hole 14 while closing the air path. At this time, when the cylindrical insert member 30 is inserted into the through-hole 14 from underneath, the atmosphere side end of the cylindrical insert member 30 abuts the step 143 formed in the seal member 11, and the flange portion 33 is engaged with the circular recess 144 formed at the lower end of the seal member 11 (see FIG. 4). As a result, the cylindrical insert member 30 and the air permeable filter 40 are positioned within the through-hole 14, and an atmosphere side face 41 of the air permeable filter 40 is located within the seal member 11.

While the thus assembled seal unit 10 is disposed within the opening end portion 61 of the cylindrical member 6, the cylindrical member 6 is crimped radially inward so as to grip the body 12 of the seal member 11. Thus, the cylindrical member 6 and the seal member 11 come into close contact with each other to thereby be reliably sealed against each other. While the air permeable filter 40 is permeable to air and impermeable to water, air is introduced into the reference gas space from the atmosphere via the air path formed in the cylindrical insert member 30.

As described above, in the oxygen sensor 1 of the present embodiment, the atmosphere side opening portion of the cylindrical insert member 30 is retracted from the end surface of the seal member 11, which is exposed to the atmosphere, toward the interior of the through-hole 14, whereby the atmosphere side face 41 of the air permeable filter 40 is located within the seal member 11; i.e., retracted from the end surface of the seal member 11.

Thus, the seal member 11 intercepts high pressure water or a flipped stone directed toward the air permeable filter 40 from the outside, thereby preventing its direct impingement on the air permeable filter 40. Further, the seal member 11 alleviates an impact force upon impingement of high pressure water or a flipped stone thereon. Thus, breakage of the air permeable filter 40 disposed within the seal member 11 can be effectively prevented. Therefore, the air permeable filter 40 can favorably maintain impermeability to water, oil and the like and air permeability, thereby ensuring reliability of the oxygen sensor 1.

In the above-described first embodiment gas sensor 1, the cylindrical insert member 30 is fixedly disposed within the seal member 11, whereby the air permeable filter 40 is disposed within the through-hole 14 to thereby be protected by means of the seal member 11.

However, since a recess is defined by the atmosphere side face 41 of the air permeable filter 40 and the wall of the through-hole 14, depending on the size of the small hole 142, water, oil or the like may accumulate in the recess, resulting in a failure to maintain air permeability of the air permeable filter 40.

Figure 6:
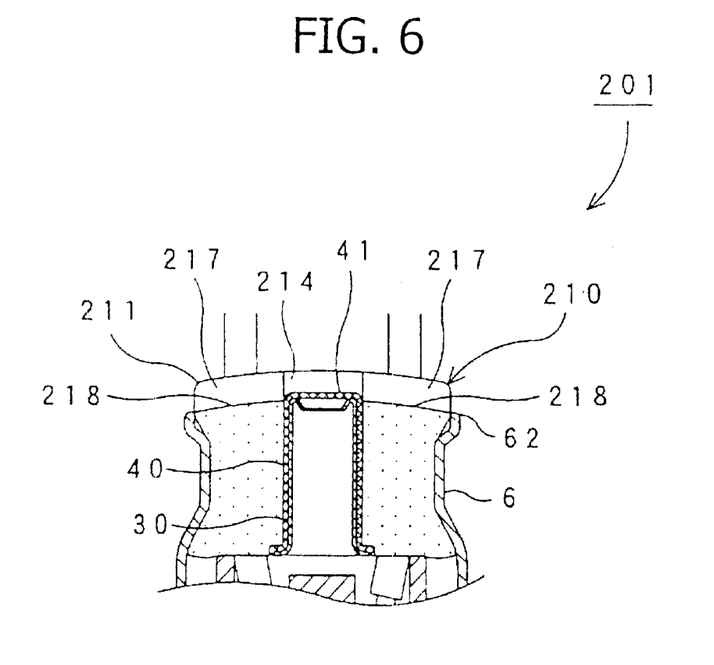
FIG. 6 is a full, sectional view of a seal unit and its periphery of an oxygen sensor according to a second embodiment of the present invention.

The second embodiment provides a solution to the above problem. FIG. 6 is a sectional view showing a seal unit 210 and its periphery of an oxygen sensor 201 according to a second embodiment of the present invention. The oxygen sensor 201 of the second embodiment differs from the oxygen sensor 1 of the first embodiment only in the structure of the seal unit. Other structural features are denoted by common reference numerals, and repeated description thereof is therefore omitted.

Figure 7:
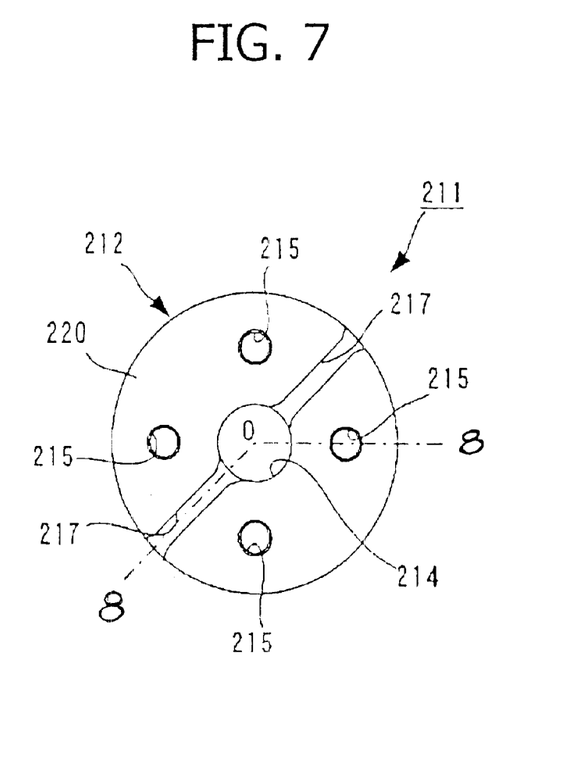
FIG. 7 is a plan view of a seal member of the seal unit of FIG. 6.

As shown in FIG. 6, the seal unit 210 of the oxygen sensor 201 includes a seal member 211, the cylindrical insert member 30, and the air permeable filter 40. The shape of the seal member 211 differs from that of the first embodiment. FIG. 7 is a plan view of the seal member 211, and FIG. 8 is a sectional view taken along line 8—8 of FIG. 7.

Figure 8:
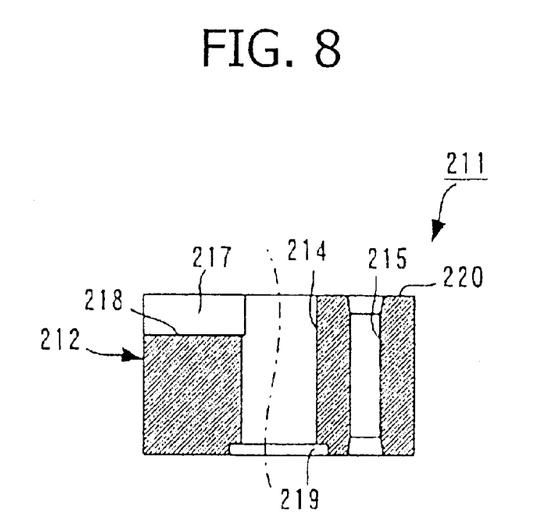
FIG. 8 is a full, sectional view of the seal member taken along line 8—8 of FIG. 7.

As shown in FIGS. 7 and 8, the seal member 211 has a columnar body 212. A through-hole 214 is formed in the body 212 in such a manner as to extend therethrough along the axis of the seal member 211. The height (thickness) of the body 212 is equivalent to the total height of the body 12 and the protrusion 13 of the seal member 11 in the first embodiment. As shown in FIG. 6, the seal member 211 protrudes from the cylindrical member 6 by a predetermined amount. Four lead passage holes 215 are formed in the body 212 while being arranged at equal intervals along a predetermined circle concentric with the through-hole 214, for allowing the lead wires 21 and 22 and the paired lead wires mentioned previously to pass therethrough.

The through-hole 214 has a diameter substantially equal to the outside diameter of the cylindrical insert member 30, as measured along the overall length thereof. An upper end portion of the through-hole 214 communicates with two drain grooves 217 extending radially on an atmosphere side face 220 of the seal member 211.

The two drain grooves 217 extend radially outward from the through-hole 214 in a symmetrical condition while passing midpoints between the two adjacent lead passage holes 215. The width of the drain grooves 217 is less than the diameter of the through-hole 214 as measured along the overall length thereof, and gradually expands where the drain grooves 217 merge into the through-hole 214. As shown in FIG. 6, the depth of the drain grooves 217 is determined such that, when the seal member 211 is attached to the cylindrical member 6, bottom surfaces 218 of the drain grooves 217 are flush with or slightly higher (biased toward the atmosphere) than an upper end 62 of the cylindrical member 6 and are lower (biased toward the reference gas space) than the atmosphere side face 41 of the air permeable filter 40 inserted in the through-hole 214.

Further, a circular recess 219 having a diameter greater than that of the through-hole 214 is formed at a reference gas side opening portion of the through-hole 214. The cylindrical insert member 30 inserted into the through-hole 14 from underneath is fitted in the seal member 211 while being engaged with the circular recess 219.

As described above, in the oxygen sensor 201 of the present embodiment, the drain grooves 217 formed on the atmosphere side face 220 of the seal member 211 extend from the periphery of the atmosphere side face 41 of the air permeable filter 40, and are located slightly lower than the atmosphere-side face 41.

Thus, water or oil adhering to the air permeable filter 40 can be drained out in an enhanced manner. Therefore, there is not much need for decreasing the diameter of an upper end portion of the through-hole 214 in contrast to the first embodiment, and the size of the atmosphere side face 41 of the air permeable filter 40 can be increased. As a result, the air permeable filter 40 can maintain good air permeability, and thus the oxygen sensor 201 can maintain good performance. Further, the seal member 211 alleviates an impact force upon impingement of high pressure water or a flipped stone thereon, thereby effectively preventing breakage of the air permeable filter 40 disposed within the seal member 211.

While the present invention has been described with reference to the first and second embodiments, the present invention is not limited thereto, but may be modified as appropriate without departing from the spirit or scope of the invention.

For example, the above second embodiment is described while mentioning the two drain grooves 217 formed on the atmosphere side face 220 of the seal member 211. However, drain grooves may be formed in such a manner as to extend radially while passing all intermediate positions between the two adjacent lead passage holes 215 (i.e., four intermediate positions), or more drain grooves may be formed, thereby enhancing the function of drain grooves for drainage of water or oil. However, an increase in the number of drain grooves weakens the strength of an upper end portion of the seal member 211, potentially resulting in a failure to sufficiently absorb an external impact force. Therefore, the number of drain grooves must be determined appropriately in view of strength and water/oil drainage performance.

In the first embodiment, radially extending drain grooves may be formed on the protrusion 13 of the seal member 11 in such a manner as to communicate with the small hole 142, thereby yielding the function of drainage of water/oil similar to that of the second embodiment.

According to the first embodiment, the cylindrical insert member 30 inserted into the through-hole 14 of the seal member 11 from underneath is caused to abut the step 143 and engage the circular recess 144 (see FIG. 4). However, since the cylindrical insert member 30 can be fitted in place in the seal member 11 merely through abutment against the step 143, the circular recess 144 may be omitted.

The above embodiments are described while mentioning the seal member having a single through-hole formed therein for introduction of air. However, a plurality of through-holes may be formed in the seal member while the air permeable filter and the cylindrical insert member are disposed in each of the through-holes. In this case, even when any one of the through-holes is blocked with a water droplet or an oil droplet, air permeability can be maintained by means of the remaining through-holes.

Figure 10:
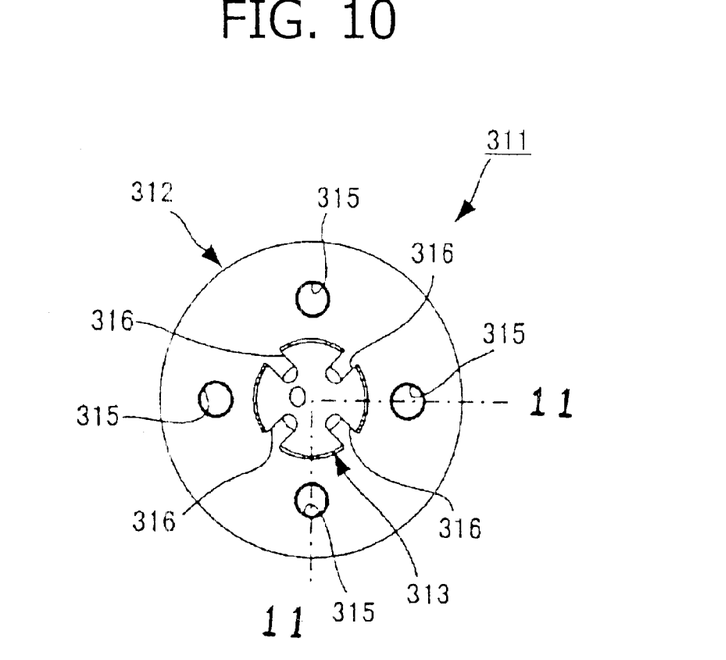
FIG. 10 is a plan view of a seal member of a seal unit according to a modification of the first embodiment.
Figure 11:
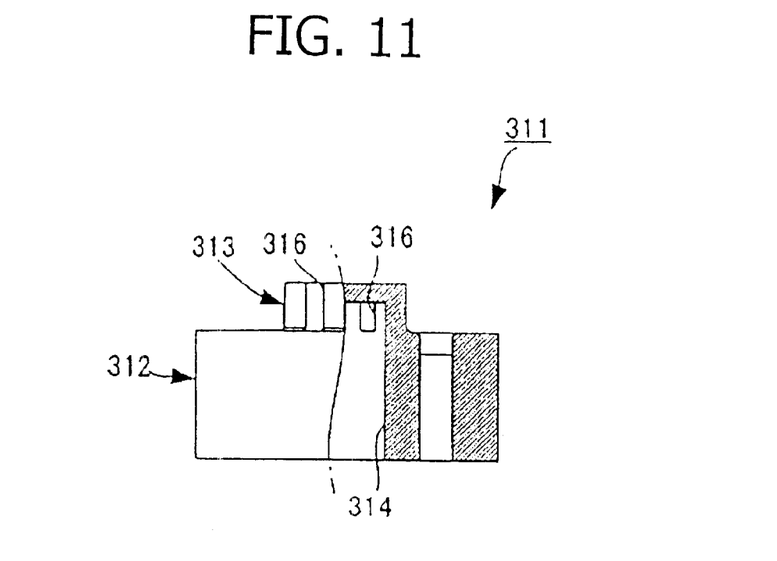
FIG. 11 is a partially sectional view of the seal member taken along line 11—11 of FIG. 10.

In a modification of the first embodiment, a seal member 311 as shown in FIGS. 10 and 11 is employed. FIG. 10 is a plan view showing the seal member 311, and FIG. 11 is a partially sectional view showing the seal member 311 (a sectional view taken along line 11—11 of FIG. 10).

The seal member 311 includes a columnar body 312 and a protrusion 313, which protrudes from the upper face of the body 312 along the axis of the seal member 311. The seal member 313 differs from the seal member 11 of the first embodiment in that the diameter of the protrusion 313 is smaller, and a plurality of breathing grooves 316 are formed on the side wall of the protrusion 313 while extending to the upper face of the protrusion 313. Each of the breathing grooves 316 is located between two adjacent lead passage holes 315 and communicates with a through-hole 314 which receives the air permeable filter and the cylindrical insert member.

The thus-modified first embodiment can function as effectively as does the first embodiment.

What is claimed is:

1. A gas sensor comprising:
   an elongated detection element for detecting a component of a gas;
   a casing for holding said detection element in such a manner as to expose a longitudinally distal end of said detection element to the gas, said casing forming a reference gas space around a longitudinally proximal end of said detection element;
   a seal member forming the reference gas space together with said casing and having an end surface exposed to the atmosphere and a through-hole for establishing communication between the atmosphere and the reference gas space;
   a cylindrical insert member inserted in the through-hole of said seal member and having an atmosphere side opening portion located on a side toward the atmosphere and a reference gas side opening portion located on a side toward the reference gas space; and
   a sheetlike air permeable filter sandwiched between an inner surface of the through-hole of said seal member and an outer surface of said cylindrical insert member, and covering the atmosphere side opening portion of said cylindrical insert member;
   wherein the atmosphere side opening portion of said cylindrical insert member is retracted from the end surface of the seal member toward the interior of the through-hole of the seal member, whereby an atmosphere side face of said air permeable filter is retracted from the end surface of said seal member.

2. A gas sensor according to claim 1, wherein entire said seal member is formed of an elastic body.

3. A gas sensor according to claim 1, wherein the through-hole formed in said seal member is constituted by a large hole opening to the reference gas space and having a diameter substantially equal to an outside diameter of said cylindrical insert member and a small hole opening to the atmosphere and having a diameter smaller than that of the large hole, the large hole and the small hole communicating with each other, and a step being formed between the large hole and the small hole; and
   said cylindrical insert member abuts the step.

4. A gas sensor according to claim 3, wherein said seal member has a protrusion axially protruding from an atmosphere side end face thereof; and
   the atmosphere side opening portion of said cylindrical insert member is inserted into the protrusion.

5. A gas sensor according to claim 2, wherein the through-hole formed in said seal member is constituted by a large hole opening to the reference gas space and having a diameter substantially equal to an outside diameter of said cylindrical insert member and a small hole opening to the atmosphere and having a diameter smaller than that of the large hole, the large hole and the small hole communicating with each other, and a step being formed between the large hole and the small hole; and said cylindrical insert member abuts the step.

6. A gas sensor according to claim 5, wherein said seal member has a protrusion axially protruding from an atmosphere side end face thereof; and the atmosphere side opening portion of said cylindrical insert member is inserted into the protrusion.

7. A gas sensor according to claim 1, wherein one or more drain grooves are formed on the atmosphere side end face of said seal member in such a manner as to extend radially outward from the periphery of the atmosphere side face of said air permeable filter, so as to drain radially outward water or oil adhering to the atmosphere side face.

8. A gas sensor according to claim 7, wherein a bottom surface of said drain groove is located in such a manner as to be biased toward the reference gas space in relation to the atmosphere side face of said air permeable filter.

9. A gas sensor according to claim 2, wherein one or more drain grooves are formed on the atmosphere side end face of said seal member in such a manner as to extend radially outward from the periphery of the atmosphere side face of said air permeable filter, so as to drain radially outward water or oil adhering to the atmosphere side face.

10. A gas sensor according to claim 9, wherein a bottom surface of said drain groove is located in such a manner as to be biased toward the reference gas space in relation to the atmosphere side face of said air permeable filter.

* * * * *